United States Patent [19]

Sugie

[11] Patent Number: 4,861,904

[45] Date of Patent: Aug. 29, 1989

[54] SCHIFF BASE METAL COMPLEX COMPOUNDS, AND ORGANOMETALLIC ULTRATHIN FILM COMPOSED THEREOF AND OXYGEN SEPARATION FILMS COMPOSED THEREOF

[75] Inventor: Kiyoshi Sugie, Iwakuni, Japan

[73] Assignee: Agency of Industrial Science and Technology, Japan

[21] Appl. No.: 26,896

[22] Filed: Mar. 17, 1987

[30] Foreign Application Priority Data

Apr. 17, 1986 [JP] Japan .................................. 61-87133
Jun. 20, 1986 [JP] Japan ................................ 61-142720
Oct. 8, 1986 [JP] Japan ................................ 61-238020

[51] Int. Cl.$^4$ ........................... C07F 1/08; C07F 3/06; C07F 13/00; C07F 15/06
[52] U.S. Cl. ......................... 556/32; 556/34; 528/9
[58] Field of Search ................... 556/32, 34

[56] References Cited

U.S. PATENT DOCUMENTS 3,472,876 10/1969 Klein ..................................... 556/32
4,044,036 8/1977 Hari ...................................... 556/32
4,113,759 9/1978 Papenfuhs ............................ 556/32

*Primary Examiner*—Michael L. Shippen
*Attorney, Agent, or Firm*—Sherman & Shalloway

[57] ABSTRACT

A Schiff base metal complex compound represented by formula (I)

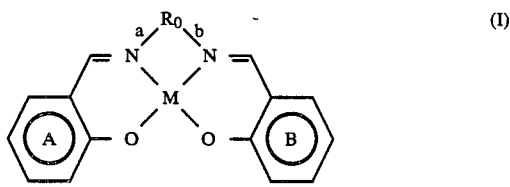

wherein
 rings A and B each denote an o-phenylene or o-naphthylene group having at least one long-chain hydrocarbon group represented by formula —X—$C_nH_m$ ($14 \leq n \leq 22$, $21 \leq m \leq 45$) in which X denotes a binding group between —$C_nH_m$ *l and the ring A or B, such as* —O—, —COO—, —NHCO— *or* —S—,
 $R_0$ denotes a hydrocarbon group having not more than 6 carbon atoms, whose adjacent carbon atoms or adjacent carbon atoms via one carbon atom are bound to bonds a and b, and
 M denotes a metal selected from the group consisting of Fe, Co, Cu, Ni, Mn, Cr and Zn, an organometallic ultrathin film composed mainly of said compound, an oxygen separation film having a layer composed mainly of said compound and a process for producing the same.

1 Claim, 1 Drawing Sheet

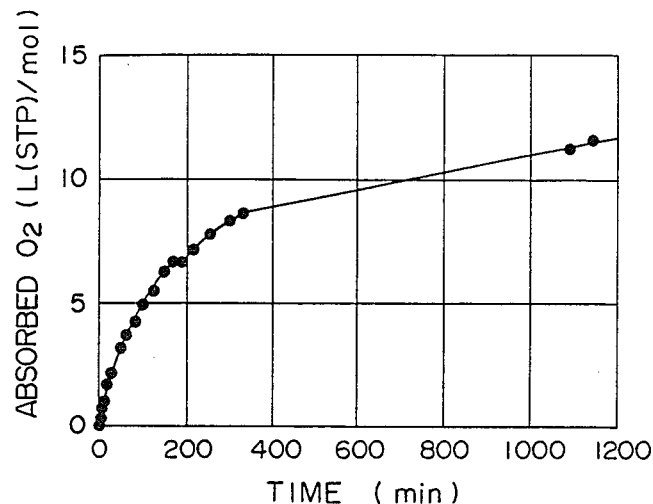
FIG. 1 OXYGEN ABSORPTION OF Co(SO-Salen) PYRIDINE SOLUTION
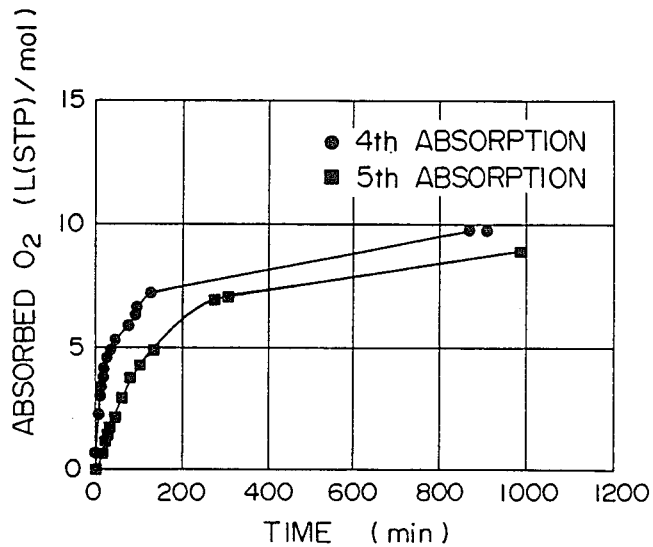
FIG. 2 OXYGEN ABSORPTION OF Co(SO-Salen) DMF SOLUTION

SCHIFF BASE METAL COMPLEX COMPOUNDS, AND ORGANOMETALLIC ULTRATHIN FILM COMPOSED THEREOF AND OXYGEN SEPARATION FILMS COMPOSED THEREOF

FIELD OF THE INVENTION

This invention relates to a novel Schiff base metal complex compound, an organometallic ultrathin film composed of said compound and a oxygen separation film composed of said compound. More specifically, it relates to a novel process for producing an organometallic ultrathin film.

DESCRIPTION OF THE PRIOR ART

An attempt has been hitherto made to synthesize compounds having an ability to absorb and desorb oxygen, similar to oxygen carriers in organisms that reversibly absorb and desorb oxygen molecules, such as hemoglobin and myoglobin. Porphyrin metal complexes, Co(Salen) complexes, etc. are examined as models for oxygen carriers of materials of separating oxygen from air.

However, these conventional metal complexes have defects that (1) irreversible oxidative degradation via dimerization tends to occur about room temperature, (2) oxidative degradation tends to occur in the presence of a small amount of water, and (3) an oxygen absorption efficiency at about room temperature is poor. The defects are great problems in utilizing these complexes. To remedy the problems, J. P. Collman et al. J. Am. Chem. Soc. 1975, vol. 97, p. 1427 discloses a method wherein dimerization is prevented by introducing a bulky substituent into a compound itself as in Picket-fence porphyrin, but this is still unsatisfactory and its concrete usage is not yet examined.

Meanwhile, as an attempt to utilize these metal complexes as oxygen carriers, a method whrein liposomes are formed by ultrasonic treatment using mixtures of phospholipids and haems to disperse the haemis in lipid films of the liposomes and develop oxygen absorbability in the aqueous solution is disclosed in E. Tsuchida: Biochem. Biophys. Res. Commun. vol. 104, p. 793 (1982) and vol. 105, p. 1416 (1982). However, this method also inevitably causes degradation by dimerization of haems before formation of the liposomes; strict treatment in an oxygen-free atmosphere is needed and prevention of the degradation is not enough.

In the circumstances, it has been long demanded to develop materials having better ability to absorb and desorb oxygen and free from degradation, and to produce ultrathin films that find concrete use in gas separation films and artificial lungs, etc.

SUMMARY OF THE INVENTION

A first object of this invention is to provide a material having excellent ability to absorb and desorb oxygen and free from degradation.

A second object of this invention is to provide an excellent oxygen separation film.

A third object of this invention is to provide an organometallic ultrathin film having excellent ability to absorb and desorb oxygen and free from degradation.

In accordance with this invention, the first object can be achieved b a Schiff base metal complex compound represented by formula (I)

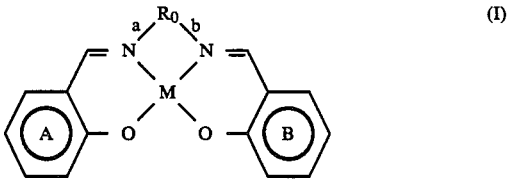

wherein
rings A and B each denote an o-phenylene or o-naphthylene group having at least one long-chain hydrocarbon group represented by formula $-X-C_nH_m$ ($14 \leq n \leq 22$, $21 \leq m \leq 45$) in which X denotes a binding group between $-C_nH_m$ and the ring A or B, such as $-O-$, $-COO-$, $-NHCO-$ or $-S-$, $R_0$ denotes a hydrocarbon group having not more than 6 carbon atoms, whose adjacent carbon atoms or adjacent carbon atoms via one carbon atom are bound to bonds a and b, and M denotes a metal selected from the group consisting of Fe, Co, Cu, Ni, Mn, Cr and Zn.

The second object can be achieved by an oxygen separation film having at least one layer composed mainly of said Schiff base metal complex compound or Schiff base metal complex units.

The third object can be achieved by using a process which comprises spreading an acyclic multidentate compound represented by formula (II)

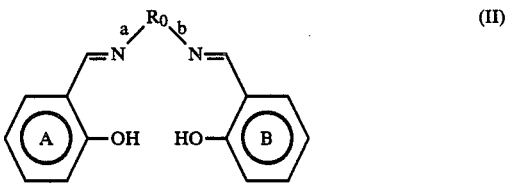

wherein
rings A and B each denote an o-phenylene or o-naphthylene group having at least one long-chain hydrocarbon group represented by formula $-X-C_nH_m$ ($14 \leq n \leq 22$, $21 \leq m \leq 45$) in which X denotes a binding group between $-C_nH_m$ and the ring A or B, such as $-O-$, $-COO-$, $-NHCO-$ or $-S-$, and $R_0$ denotes a hydrocarbon group having not more than 6 carbon atoms, whose adjacent carbon atoms or adjacent carbon atoms via one carbon atom are bound to bonds a and b, on the surface of an aqueous phase; and either after or before compression, supplying a metallic ion from the aqueous phase to form a chelete ring with the metallic ion.

The Schiff base metal complex compound of this invention is a complex of a central metal in low valence and a ligand of a Schiff base compound.

The central metal of the Schiff base metal complex compound in this invention is a transition metal of low valence selected from the group consisting of iron, cobalt, copper, nickel, manganese, chromium and zinc. Iron and cobalt are most preferable.

Rings A and B in formula (1) are each an o-phenylene or o-naphthylene group having at least one long-chain hydrocarbon group represented by formula $-X-C_nH_m$ ($14 \leq n \leq 22$, $21 \leq m \leq 45$) in which X denotes a binding group between —$C_nH_m$ and the ring A or B, such as —O—, —COO—, —NHCO— or —S—. —$C_nH_m$ is an alkyl, alkenyl or alkynyl group having 14 to 22 carbon atoms. Concrete examples thereof are alkyl groups such as tetradecyl, pentadecyl, hexadecyl, heptadecyl, octadecyl, docosyl, etc., branched alkyls such as isostearyl, et al., and linear unsaturated hydrocarbon groups such as cis-9-hexadecenyl, cis-9-cis-12-octadecadienyl, octadeca-10,12-diyl, etc. However, these are not limitative. Preferable of these are hexadecyl, octadecyl, eicosyl, docosyl, trans-2-octadecenyl, cis-9-ocadecenyl, pentadeca-2,4-diyl, heptadeca-2,4-diyl and tricosa-10,12-diyl.

$R_0$ denotes a hydrocarbon group having not more than 6 carbon atoms, whose adjacent carbon atoms or adjacent carbon atoms via one carbon atom are bound to bonds a and b. Preferable is a hydrocarbon group whose carbon atoms are directly adjacent each other.

Concrete examples of Ro are —$CH_2CH_2$—, —$CH_2$—$CH_2$—$CH_2$—, —$CH(CH_3)CH_2$—, —$CH_2C(CH_3)_2$—, —$CH(CH_3)$—$CH(CH_3)$—, —$C(CH_3)_2C(CH_3)_2$, —$CH(C_2H_5)CH_2$—, —$CH(C_2H_5)CH(C^2H_5)$—, —$CH_2C(C_2H_5)_2$

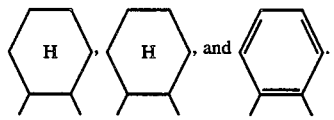

Preferable are —$CH_2CH_2$—, —$CH_2C(CH_3)_2$—,

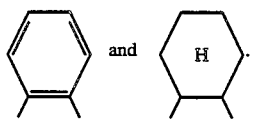

The Schiff base metal complexes in this invention can be obtained by, for example, reacting salicylaldehyde derivatives with diamines to form Schiff bases and introducing metals of low valence into said Schiff bases.

When use as an oxygen absorbent, said Schiff base metal complexes may be employed in powder form as such or in particulte or pellet form or in solution.

The Schiff base metal complex bonding units in the oxygen separation film of this invention mean recurring units of a polymer resulting from a polymerization reaction of the Schiff the metal complex compound represented by formula (1).

The oxygen separation film in this invention has at least one layer composed mainly of the Schiff base metal complex compound or the Schiff base metal complex binding units. Such layer may be formed from the Schiff base metal complex compound or the polymer having the Schiff base metal complex binding units directly by a casting method, a spin coating method, or a method for making a monomolecular film (e.g. a LB method). As will be later described, it may also be produced by making the thin film and then coordinating the metal or conducting the polymerization reaction.

In this invention, other compounds than the complex compound or the complex binding units, which may be present to aid in layer (film) formation, are e.g. carboxylic acids having a long-chain alkyl, alkenyl or alkynyl group having 14 to B 24 carbon atoms, esters, amines, amides, ureas and alcohols.

Concrete examples thereof are myristic acid, palmitic acid, stearic acid, arachic acid, behenic acid, petroselinic acid, oleic acid, etc., and their esters and amide derivatives; tetradecylamine, stearylamine, etc. and their amide and urea derivatives; tetradecanol, octadecanol, eicosanol, docosanol, etc. and their ester derivatives, and so forth.

The proportion of these compounds is not more than 20%, preferably not more than 10%.

In order to stabilize the complexes and improve the ability to absorb and desorb oxygen in this invention, compounds capable of coordinating with the complex may be added to the complex. Examples of such compounds are pyridine, 4-methylpyridine, 4-aminopyridine, 4-t-butylpyridine, 4-cyanopyridine, 3,4-lutidine, quinoline, imidazole, benzimidazole, N-methylimidazole, dimethylformamide, dimethylsulfoxide, oxazole, thiazole and pyrrole.

The complexes to which these compounds have been added may be used directly s an oxygen absorbent or as an oxygen separation film in layer (film) form.

Particularly in the oxygen separation film of this invention, another film can be laminated on a film (layer) composed of said complex for stabilizing the complex and improving the ability to absorb and desorb oxygen. Such film is made of a film-forming compound capable of coordinating with the complex. Examples of said compound are 4-octadecylpyridine, N-dodecylimidazole, 4-palmitoylaminopyridine, 4-octadeclquinoline, 2- octadecylimidazole, 2-eicosyloxazole and 2-docosylthiazole.

A most preferable process for producing an organometallic ultrathin film or an oxygen separation film in this invention comprises spreading an acyclic multidentate compound represented by formula (II)

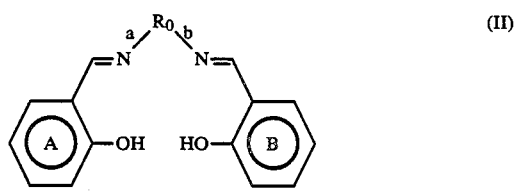

(II)

wherein
rings A and B each denote an o-phenylene or o-naphthylene group having at least one long-chain hydrocarbon group represented by formula —X—$C_nH_m$ ($14 \leq n \leq 22$, $21 \leq m \leq 45$) in which X denotes a binding group between —$C_nH_m$ and the ring A or B, such as —O—, —COO—, —NHCO— or —S—, and
$R_0$ denotes a hydrocarbon group having not more than 6 carbon atoms, whose adjacent carbon atoms or adjacent carbon atoms via one carbon atom are bound to bonds a and b, on the surface of an aqueous phase, and either after or before compression, supplying a metallic ion from the aqueous phase to form a chelete ring with the metallic ion.

Said acyclic multidentate compound is such that two or more coordination sites exist and a line obtained by joining the sites does not form a loop.

A method of forming a thin film of an organic compound on the surface of the aqueous phase is generally known and performed by spreading a suitable amount of a solution of an organic compound dissolved in a volatile solvent substantially immiscible with the aqueous phase on the surface of the aqueous phase and volatilizing the solvent. In the process of this invention, a suitable amount of a solution of the amphiphilic acyclic multi-dentate compound in a volatile solvent immiscible with an aqueous phase is spread on the surface of the aqueous phase, and the solvent is then volatilized. It is at times advantageous to use a mixture of some organic solvents. In case the most suitable solvent for a specific acyclic multidentate compound is water-miscible, it can commonly be used in admixture with another water-immiscible solvent.

A metallic ion may be charged in the aqueous phase either before or after spreading the solution of the acyclic multidentate compound, or either before or after compression. By supplying the metallic ion, the acyclic multidentate compound forms a chelate ring by a chelate reaction with the metallic ion to provide a rigid film.

Examples of the metallic ion are those described as chelete-forming metals in e.g. "Chemistry of the Metal Chelate Compounds" b A. E. Martell and M. Carbin. Most preferable metallic ions are Cu, Ni, Co, Zn, Fe, Mn and Cr.

These metallic ions can be added to the aqueous phase in varying salt forms. Examples of the salts are acetates, hydrochlorides, sulfates and phosphates.

According to the process of this invention, a monomolecular layer of the chelate compound with molecules oriented substantially uniformly is formed on the surface of the aqueous phase. When compressed before chelating, a monomolecular layer of the acyclic multidentate compound is commonly degraded. However, the monomolecular layer made by this invention becomes a rigid condensed film via compression, providing a LB film.

Since in such film-forming process the chelated compounds are aligned on the surface of the aqueous phase as monomolecular layers, the chelete surfaces are not opposite to each other, making it possible to achieve a great secondary effect that degradation by dimerization is preventable.

Moreover, as the chelate compounds formed from the acyclic multidentate compounds have hydrophobic groups and are thus hard to crystallize, purification thereof is difficult. Even if said compounds can be purified, they are close to each other, therefore easy to dimerize and prone to degradation. Nevertheless, in this invention, purification may be conducted before chelating and is easy, and degradation does not occur because there is no step which easily allows dimerization as noted above.

The organometallic ultrathin film of this invention may also be obtained by forming a thin film of a precursor of the Schiff base metal complex bonding units and then conducting polymerization. It can be achieved by using long-chain linear unsaturated hydrocarbon groups such as cis-9-hexadecenyl, cis-9-cis-12-octadecadienyl and octadeca-10,12-diyl and exposing to energy rays such as electron rays and ultraviolet rays.

In the oxygen separation film of this invention, a support can be used to make up for lack of a self-supporting property of the Schiff base metal complex thin film. Examples of such support are porous supports made of metals, glasses, ceramics, and synthetic and natural polymers. The form thereof can be optionally selected from a sheet, a plate, a spiral mode, a tube and hollow fibers depending on the purpose. Most preferable are polymer porous materials such as a polyethylene porous film, a polypropylene porous film, a cellulose ultrafilter, a polycarbonate porous film, a polysulfone ultrafilter and a polyvinylidene fluoride porous film. Moreover, for improvement of adhesion and surface smoothness, the surfaces of these supports may be modified too.

When the Schiff base metal complex afforded in this invention is contacted with oxygen as a powdery solid or in a solution or suspension containing an inert solvent such as benzene, toluene, chloroform or methylene chloride or a coordination solvent such as dimethylformamide, dimethylsulfoxide, pyridine or imidazole, it absorbs oxygen rapidly at room temperature and an atmospheric pressure. Oxygen absorbed can easily be desorbed by placing an oxygen absorbent that has absorbed oxygen under reduced pressure or heating it. Said complex is thus available as an oxygen absorbent.

The oxygen separation film in this invention lends itself to condensation of oxygen from air in particular.

The following Examples illustrate this invention. However, this invention is not limited to said Examples.

Example 1: Synthesis of bis(2-hydroxy-4-octadecyl-oxybenzal) ethylenediimine, ($H_2$(SO-Salen))

1.95 g of 2-hydroxy-4-octadecyl-oxybenzaldehyde was dissolved in 30 ml of pyridine, and a solution of 0.15 g ethylenediamine in 10 ml pyridine was added thereto dropwise. With stirring, the mixture was heated to 60° C. and the reaction was run for 1 hour. After the mixture was left to cool, a precipitate was filtered, and the filtrate was washed with ethanol and then vacuum dried to obtain a pale yellow needle crystal.

| | |
|---|---|
| NMR 0.88 ppm | $CH_3$ |
| 1.25, 1.76, 3.83, 3.94 | $CH_2$ |
| 6.36, 6.40, 7.05 | benzene ring |
| 8.18 | CH |
| 13.61 | OH |
| IR 2919 $cm^{-1}$ | $v_{C-H}$, as |
| 2850 | $v_{C-H}$, s |
| 1629 | $v_{C=N}$ |

In MS spectrum, a molecular ion peak of M/e=804 was observed and formation of $H_2$ (SO-Salen) was thus ascertained.

Example 2: Synthesis of bis(2-hydroxy-4-octadecyl-oxybenzal)ethylenediimine cobalt (Co(SO-Salen)) 1.00 g of $H_2$(SO-Salen) was dissolved in 50 ml of pyridine, and a solution of 0.309 g Co($CH_3$COO)$_2$.4$H_2$O in 25 ml of pyridine was added thereto dropwise. With stirring, the mixture was reacted for 3 hours under reflux. After pyridine was distilled off and the residue was evaporated to dryness, the product was dissolved again in chloroform and washed with water to remove an unreacted material and by-products. Chloroform was distilled off to afford a reddish black solid.

IR spectrum and elemental analysis of the solid are:

| | |
|---|---|
| IR 2921 $cm^{-1}$ | $v_{C-H}$ as |
| 2851 | $v_{C-H}$, s |
| 1606 | $v_{C=N}$ |
| Elemental analysis: | Co(SO-salen) |
| | Calc.; H:C:N:Co = 10.1:72.4:3.3:6.8 |

-continued

Obs.; H:C:N:Co = 10.0:71.4:3.2:7.0

Formation of Co(SO-Salen) was thus ascertained.

Example 3: Synthesis of 1,2-bis(2-hydroxy-4-octadecyloxy-benzal)phenylenediimine H₂(SO-Salphn))

1.95 g of 2-hydroxy-4-octadecyl-oxybenzaldehyde was dissolved in 30 ml of pyridine, and a solution of 0.27 g o-phenylenediamine in 10 ml of pyridine was added thereto dropwise. With stirring, the mixture was heated to 60° C. and reacted for 1 hour. Pyridine was distilled off and the residue was evaporated to dryness. Recrystallization from ethanol gave a yellow branch-like crystal.

NMR and IR spectra of the product are:

| NMR 0.87 ppm | $CH_3$ |
|---|---|
| 1.25, 1.78, 3.97 | $CH_2$ |
| 6.41, 6.51, 7.19–7.28 | benzene ring |
| 8.53 | CH |
| 13.57 | OH |
| IR 2920$^{cm-1}$ | $\nu_{C-H}$, as |
| 2851 | $\nu_{C-H}$, s |
| 1614 | $\nu_{C=N}$ |

Formation of H₂(SO-Salphn) was thus ascertained.

Example 4: Synthesis of 1,2-bis(2-hydroxy-4-octadecyloxy-benzal)phenylenediimine cobalt (Co(SO-Salphn))

The procedure in Example 2 was repeated in the same way as in Example 2 except that 0.91 g of H₂(SO-Salphn) was used instead of 1.00 g of H₂(SO-Salen) and the amount of Co(CH₃COO)HD 2.4H₂O was changed from 0.309 g to 0.25 g. There resulted a reddish black solid of Co(SO-Salphn).

Example 5: Use of Co(So-Salen) as an oxygen absorbent 0.580 g of Co(SO-Salen) obtained in Example 2 was dissolved in 50 ml of pyridine, and the solution was freezed and degassed. The solution was put on a gas burette in a constant temperature box of 30° C. and contacted with oxygen of an atmospheric pressure. As a result, it absorbed 11.6 l (STP)/mol as shown in FIG. 1 attached hereto. After pyridine was distilled off, the residue was dissolved again in DMF, and absorption and desorption of oxygen were repeated. Thus, reversibility was evaluated as shown in FIG. 2 attached hereto. From FIG. 2, it became apparent that Co(SO-Salen) had excellent reversibility to absorb and desorb oxygen.

Example 6

0.597 g of Co(SO-Salphn) obtained in Example 4 was evacuated in solid state as such, and put on a gas burette in a constant temperature box of 30+ C. and contacted with oxygen of an atmospheric pressure. It absorbed 6.7 l (STP)/mol of oxygen. Subsequently, the sample was dissolved in 50 ml of pyridine, and oxygen absorbability was evaluated as in Example 5. As a result, an amount of oxygen absorbed was 3.8 l (STP)/mol.

Example 7

A trough fitted with a stationary barrier, a movable barrier moved by a drive device was filled with a cobalt acetate aqueous solution ($5 \times 10^{-5}$ mol/l) as an aqueous phase. 4.4 mg of bis(2-hydroxy-4-octadecyl-oxybenzal)ethylenediimine was dissolvd in 10 ml of chloroform, and 200 microliters of the solution was spread on the surface of the aqueous phase. The molecules remaining on the aqueous phase after evaporation of the solvent were left to stand for 30 minutes. Then the movable barrier was moved at a rate of 0.2 mm/S. While the monomolecular film was compressed, change in surface pressure to an area surrounded by the stationary barrier, the movable barrier and both ends of the trough was measured. A rising portion of a pressure shows a compression ratio $$\left( Cs = -\frac{1}{A} \frac{\partial A}{\partial \pi} \right) \text{ of } 0.0096,$$

and it revealed formation of a condensed film. Moreover, the film could be placed on a glass plate by vertically moving the glass plate across the film plate while maintaining the pressure at 25 mN/m.

Comparative Example

Area-pressure change was examined in the same way as in Example 7 except using pure water as an aqueous phase.

Though the pressure once started to rise, it lowered again and degradation of the film occurred. This film could not be moved onto a glass substrate in complete form.

Example 8

A trough fitted with a stationary barrier, a movable barrier moved by a drive device and a pressure sensor to measure a surface pressure was filled with a cobalt acetate aqueous solution ($5 \times 10^{-5}$ mol/l) as an aqueous phase.

4.6 mg of 1,2-bis(2-hydroxy-4-octadecyl-oxybenzal)-phenylenediimine was dissolved in 10 ml of chloroform, and 200 microliters of the solution was spread on the surface of the aqueous phase. After it was left to stand for 30 minutes, the movable barrier was moved at a rate of 0.2 mm/S. While the monomolecular film was compressed, change in surface pressure to an area surrounded by the stationary barrier, the movable barrier and both ends of the trough was measured. A rising portion of a pressure shows a compression ratio $$\left( Cs = -\frac{1}{A} \frac{\partial A}{\partial \pi} \right) \text{ of } 0.0138,$$

and it revealed formation of a condensed film. Moreover, the film could be placed on a glass plate by vertically moving the glass plate across the film while maintaining the pressure at 25 mN/m.

Example 9

A thin coating layer of a silicon polymer was formed on a polypropylene porous film (®Celgard 2400) to afford a modified support having an oxygen permebility of $1.04 \times 10^{-4}$ cm³/cm².S.CmHg, $$\alpha \frac{O_2}{N_2} = 2.1.$$

On this support was laminated a monomolecular film made from H₂(SO-Salen) obtained in Example 1.

That is, a trough fitted with a stationary barrier, a movable barrier moved by a drive device and a pressure sensor to measure a surface pressure was filled with a cobalt acetate aqueous solution ($5\times10^{-5}$ mol/l) as an aqueous phase. 200 micoliters of a solution of 4.4 mg H₂(SO-Salen) in 10 ml chloroform was spread on the surface of the aqueous phase held at 15° C. The molecules remaining on the aqueous phase after evaporation of the solvent were left to stand for 30 minutes. Then it was compressed to 25 mN/m by the movable barrier. Twenty layers of such film were laminated by a horizontal lifting method while keeping a constant pressure (25 mN/m).

Subsequently, a thin overcoat layer of a silicon polymer was formed, and a gas selectivity and a gas permeability of the resulting composite film were evaluated. As a result, a nitrogen permeability was $2.69\times10^{-7}$ cm³/cm².S.CmHg, an oxygen permeability $9.29\times10^{-7}$ cm³/cm².S.CmHG, and a selectivity 3.5, respectively.

Example 10

11.1 g of 2,4-dihydroxybenzaldehyde was dissolved in 200 ml of isopropanol, and a solution of 2.4 g ethylenediamine in 200 ml of isopropanol was added thereto dropwise. With stirring, the mixture was reacted for 2.5 hours under reflux. After the reaction mixture was left to cool, 4.5 g of potassium hydroxide dissolved in 80 ml of methanol was added. Subsequently, a solution of 10 g cobalt acetate tetrahydrate in 45 ml water was added, and the mixture was reacted for 2.5 hours under reflux. After the reaction mixture was left to cool overight, the resulting precipitate was filtered off to obtain a blackish red needle crystal (Schiff base complex (I)).

In IR spectrum of the product, absorption of C=N was observed in the vicinity of 1530 cm⁻¹. Formation of Schiff base complex was thus ascertained. Elemental analysis of the product revealed the composition ratio, C:H:N:Co=50.2:4.0:7.2:15.2 (%)

which well corresponded to a calculated value,

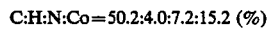

C:H:N:Co=49.4:3.6:7.2:15.1 (%).

On the other hand, 12.0 g of 2-octadecenoyl chloride was dissolved in 100 ml of benzene, and a solution obtained by dispersing 7.1 g of the above Schiff base complex in 100 ml of pyridine was added thereto dropwise. With stirring, the mixture was reacted for 3 hours under reflux. The reaction liquid was, after left to cool, washed with water, condensed and evaporated to dryness. In IR spectrum of the product, absorption of νC=O was observed in the vicinity of 1735 cm⁻¹ and absorption of νC=C in the vicinity of 1650 cm⁻¹. It was thus confirmed that an alkenyl group was introduced via an ester linkage.

0.352 g of the thus obtained Schiff base metal complex was dissolved in 50 ml of dimethylformamide, and the solution was freezed and degassed. The solution was put on a gas burette in a constant temperature box of 30° C. and contacted with oxygen of an atmospheric presure. It absorbed 6.2 ml of oxygen.

Example 11

27.6 g of 2,4-dihydroxybenzaldehyde was dissolved in 100 ml of dimethylformamide (DMF), and 6.0 g of ethylenediamine was added thereto dropwise. With stirring, the reaction was run at 120° for 5 hours. After DMF was then distilled off at 50° C. under reduced pressure, and unreacted substance and DMF were washed with ether and dried to obtain a bright yellow powder (Schiff base (I)). Elemental analysis of the product revealed the composition ratio,

C:H:N=63.41:5.29:9.50 (%)

which well corresponded to a calculated value,

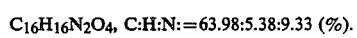

10.4 g of the resulting Schiff base (I) was dissolved in 100 ml of pyridine, and a solution of 20.8 g 2-octadecenoyl chloride in 50 ml benzene was added dropwise with ice cooling. After the addition was over, stirring further continued at room temperature for 2 hours. 250 ml of ether was added to the reaction liquid, and washing with a Na₂CO₃ aqueous solution and water was repeated. The ether layer was evaporated to dryness. The resulting product was subjected to liquid chromatography to obtain a long-chain Schiff base ligand (II). In IR spectrum of the product, absorption of νC=O was observed in the vicinity of 1750 cm⁻¹ and absorption of νC=C in the vicinity of 1660 cm⁻¹ respectively. It was thus confirmed that an alkenyl group was introduced through an ester linkage.

Example 12

A thin coating layer of silicon polymer was formed on a polypropylene porous film (® Celgard 2400) to afford a modified support having an oxygen permeability of $1.04\times10^{-4}$ cm³/cm².S.cmHg $$\alpha \frac{O_2}{N_2} = 2.1.$$

On the support was laminated a monomolecular film made from the long-chain Schiff base ligand (II) obtained in Example 11.

That is, a trough fitted with a stationary barrier, a movable barrier moved by a drive device and a pressure sensor to measure a surface pressure was filled with a cobalt acetate aqueous solution ($4.59\times10^{-1}$ mol/l) as an aqueous phase. 200 microliters of a solution of 4.6 mg long-chain Schiff base ligand (II) in 10 ml of chloroform was spread on the surface of the aqueous phase kept at 10° C. The molecules remaining on the aqueous phase after evaporation of the solvent were left to stand for 30 minutes. Then a film was compressed to 25 mN/m by the movable barrier, and 20 layers of such film were laminated b a horizontal lifting method while keeping a constant pressure (25 mN/m.

A gas selectivity and a gas permeabilty of the resulting composite film were evaluated. Consequently, a nigrogen permeability was $2.58\times10^{-6}$ cm³/cm².S.cmHg, an oxygen permeability $9.44\times10^{-6}$ cm³/cm².S.cmHg, and a selectivity 3.7 respectively.

Example 13

A monomolecular film made from the long-chain Schiff base ligand (II) obtained in Example 11 and a monomolecular film made of 4-octadecylpyridine were alternately laminated on the modified support used in Example 12.

That is, a cobalt acetate aqueous solution ($4.59 \times 10^{-3}$ mol/l) was filled as an aqueous phase. 200 microliters of a solution of 4.6 mg long-chain Schiff base ligand (II) in 10 ml chloroform was spread on the surface of the aqueous solution held at 10° C. The molecules remaining on the aqueous phase after evaporation of the solvent were left to stand for 30 minutes. Then a film was compressed to 25 mN/m. While maintaining a constant predsure (25 mN/m), the modified support was vertically dipped to penetrate the Schiff base metal complex monomolecular film formed on the surface of the aqueous phase. Subsequently, while the modified support was dipped, the film left on the surface of the aqueous phase was removed, and 200 microliters of a solution of 1.8 mg 4-octadecylpyridine in 10 ml chloroform was then spread. A film was compressed to 20 mN/m by the compression barrier, and drawn while keeping a constant pressue (20 mN/m). In like manner, dipping and drawing were repeated, and 20 Layers of the Schiff base metal complex monomolecular film were alternately laminated with 20 layers of the 4-octadecylpyridine monomolecular film.

A gas selectivity and a as permeability of the resulting composite film were evaluated. As a result, a nitrogen permeability was $3.7 \times 10^{-6}$ cm$^3$/cm$^2$.S.cmHg, an oxygen permeability $1.37 \times 10^{-5}$ cm$^3$/cm$^2$.S.cmHg, and a selectivity 3.7 respectively.

Example 14

A trough fitted with a stationary barrier, a movable barrier moved by a drive device and a pressure sensor to measure a surface pressure was charged with a cobalt acetate aqueous soluton ($4.59 \times 10^{-3}$ mol/l) as an aqueous phase. 200 μl of a solution of 4.6 mg bis(4-(2-octadecenoyl)sallicylaldehyde) ethylenediimine in 10 ml of chloroform was spread on the surface of the aqueous phase. The molecules remaining on the aqueous phase after evaporation of the solvent were left to stand for 30 minutes. Then the movable barrier was moved at a rate of 0.2 mm/S, and while the film was compressed, change in surface pressure to an area surrounded by the stationary barrier, the movable barrier and both ends of the trough was measured. A rising portion of a pressure shows a compression ratio $$\left( Cs = -\frac{1}{A} \frac{\partial A}{\partial \pi} \right) \text{of } 0.008,$$

and it revealed formation of a condensed film. Moreover, the film could be placed on a glass plate by vertically moving the glass plate across the film while maintaining the pressure at 25 mN/m.

When pure water was used as the aqueous phase, the pressure once started to rise but lowered again, causing degradation of the film. This film could not be moved onto the glass substrate in complete form.

What we claim is: L

1. A Schiff base metal complex compound represented by formula (I)

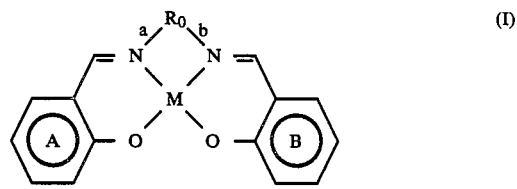

wherein ring A and B each denote an σ-phenylene or orthonaphthalene group having at least one group represented by the formula —X—C$_n$H$_m$ wherein —C$_n$H$_m$ is a long-chain alkyl, alkenyl or alkynyl hydrocarbon group, $14 \leq n \leq 22$ and $21 \leq m \leq 45$, and X represents a binding group between —C$_n$H$_m$ and the ring A or B selected from the group consisting of —O—, —COO—, —NHCO— and —S—;

R$_0$ represents a hydrocarbon group having not moe than 6 carbon atoms, whose adjacent carbon atoms or adjacent carbon atoms via one carbon atom are bound to bonds a and b; and M represents a metal selected from the group consisting of Fe, Co, Cu, Ni, Mn, Cr and Zn.

* * * * *